(12) United States Patent
Yun et al.

(10) Patent No.: US 8,247,450 B2
(45) Date of Patent: Aug. 21, 2012

(54) LINOLEIC ACID ACTIVE AGENTS FOR ENHANCING PROBABILITY OF BECOMING PREGNANT

(75) Inventors: Anthony Joonkyoo Yun, Palo Alto, CA (US); Patrick Yuarn-Bor Lee, Menlo Park, CA (US); Albert Cha, Mountain View, CA (US)

(73) Assignee: Palo Alto Investors, Palo Alto, CA (US)

( * ) Notice: Subject to any disclaimer, the term of this patent is extended or adjusted under 35 U.S.C. 154(b) by 2 days.

(21) Appl. No.: 12/826,440

(22) Filed: Jun. 29, 2010

(65) Prior Publication Data

US 2010/0280116 A1 Nov. 4, 2010

Related U.S. Application Data

(63) Continuation of application No. 11/198,003, filed on Aug. 5, 2005, now Pat. No. 7,767,713.

(60) Provisional application No. 60/599,347, filed on Aug. 5, 2004.

(51) Int. Cl.
*A01N 37/00* (2006.01)
*A61K 31/08* (2006.01)

(52) U.S. Cl. ........................ 514/560; 514/722

(58) Field of Classification Search .............. 514/560, 514/722
See application file for complete search history.

(56) References Cited

U.S. PATENT DOCUMENTS

| | | | |
|---|---|---|---|
| 4,281,064 A | 7/1981 | Suzuki et al. | |
| 4,529,551 A | 7/1985 | Cleary et al. | |
| 5,443,844 A | 8/1995 | McDaniel | |
| 5,892,074 A | 4/1999 | Seidel | |
| 6,153,774 A | 11/2000 | Seidel | |
| 6,242,621 B1 | 6/2001 | Jerome et al. | |
| 6,296,861 B1 | 10/2001 | Perricone | |
| 6,300,374 B1 | 10/2001 | Bryce-Smith | |
| 6,319,950 B1 | 11/2001 | Seidel | |
| 6,333,353 B2 | 12/2001 | Saebo et al. | |
| 6,395,782 B1 | 5/2002 | Cook et al. | |
| 6,409,649 B1 | 6/2002 | Reaney | |
| 6,410,761 B1 | 6/2002 | Saebo et al. | |
| 6,420,577 B1 | 7/2002 | Reaney et al. | |
| 6,440,931 B1 | 8/2002 | Remmereit et al. | |
| 6,524,527 B2 | 2/2003 | Fimreite et al. | |
| 6,569,857 B1 | 5/2003 | Hermelin et al. | |
| 6,608,222 B2 | 8/2003 | Bonsignore et al. | |
| 6,610,868 B2 | 8/2003 | Saebo et al. | |
| 6,743,931 B2 | 6/2004 | Sæbo et al. | |
| 6,756,405 B2 | 6/2004 | Fimreite | |
| 6,762,313 B2 | 7/2004 | Strube et al. | |
| 6,852,757 B2 | 2/2005 | Jerome et al. | |

OTHER PUBLICATIONS

Schwabe et al. "Hysterosalpingography with Oil Contrast Medium Enhances Fertility in Patients with Infertility of Unknown Etiology," Fertility and Sterility (1983) 40(5):604-606.
Mackey et al. "Pregnancy Following Hysterosalpingography with Oil and Water Soluble Dye," Fertility and Sterility (1971) 22(8):504-507.
Willis et al. "Cytokine Production by Peripheral Blood Monocytes During the Human Ovulatory Menstrual Cycle," Human Reproduction (2003) 18(6):1173-1178.
Westphal et al. "A Nutritional Supplement for Improving Fertility in Women," The Journal of Reproductive Medicine (2004) 49(4):289-293.
Liu et al. "Isolation of Linoleic Acid as an Estrogenic Compound from the Fruits of Vitex Agnus-CastusL. (chaste-berry). " Phytomedicine (2004) 11:18-23.
Wander et al. "The Ratio of Dietary (n-6) to (n-3) Fatty Acids Influences Immune System Function, Eicosanoid Metabolism, Lipid Peroxidation and Vitamin E Status in Aged Dogs [1-4]," American Society for Nutritional Sciences (1997) 127:1198-1205.
Piccini et al. "Role of Hormone-Controlled T-Cell Cytokines in the Maintenance of Pregnancy," Biochemical Society (2000) 28(2):212-215.
Lillie et al. "Effect of linoleic acid deficiency on the fertilizing capacity and semen fatty acid profile of the male chicken." Nutritions, 95: 311-315,1967.

*Primary Examiner* — Renee Claytor
(74) *Attorney, Agent, or Firm* — Bozicevic, Field & Francis LLP; Bret E. Field; David E. Eramian

(57) ABSTRACT

The present invention is directed to a methods and compositions for enhancing the probability that a subject will become pregnant. The method comprises administering to a subject a pharmaceutical composition comprising an effective amount of a linoleic acid active agent, e.g., linoleic acid, a polyunsaturated fatty acid analog thereof, etc. Also provided are kits that find use in practicing the subject methods. The subject methods and compositions find use in a variety of different applications, including but not limited to the treatment of infertility conditions.

22 Claims, No Drawings

LINOLEIC ACID ACTIVE AGENTS FOR ENHANCING PROBABILITY OF BECOMING PREGNANT

CROSS-REFERENCE TO RELATED APPLICATIONS

Pursuant to 35 U.S.C. §119 (e), this application claims priority to the filing date of U.S. Provisional Patent Application Ser. No. 60/599,347 filed Aug. 5, 2004; the disclosure of which application is herein incorporated by reference.

BACKGROUND OF THE INVENTION

Infertility is an increasingly common disease afflicting modern societies. During the $20^{th}$ century and into the $21^{st}$ century, with increasing affluence and longer lifespans, today's women have tended to marry later in life than previous generations. However, studies have determined that fertility declines with increasing age. As these is women decide to have children and attempt to become pregnant, they discover that they often have difficulties becoming pregnant. A number of these women will also seek medical care to assist their efforts in successfully becoming pregnant. This trend of the growing prevalence infertility is being reinforced by intrinsic biological shifts that occur with increasing maternal age, including changes in menstrual cycle, ovulation, uterine receptivity, and immunological changes. Currently utilized modes of therapy range from pharmacologic treatments, such as clomiphene citrate and GnRH injections, to more invasive therapies such at extraction of ova from the ovaries and in vitro fertilization. However, despite these treatment strategies, disorders of impaired fertility remain a major clinical problem.

As such, there continues to be an interest in the development of new protocol options for treating fertility conditions.
Relevant Literature Mackey et at., Pregnancy following hysterosalpingography with oil and water soluble dye. *Fertility and Sterility* 1971; 22:504-507; Schwabe et al., Hysterosalpingography with oil contrast medium enhances fertility in patients with infertility of unknown etiology. *Fertility and Sterility* 1983; 40:604-606; Willis C et al., "Cytokine production by peripheral blood monocytes during the normal human ovulatory menstrual cycle." *Human Reproduction* 2003; 18:1173-1178; Piccinni et al., "Role of hormone-controlled T-cell cytokines in the maintenance of pregnancy." *Biochemical Society Transactions* 2000; 28:212-215; Wander et al., "The ratio of dietary (n-6) to (n-3) fatty acids influences immune system function, eicosanoid metabolism, lipid peroxidation and vitamin E status in aged dogs." *Journal of Nutrition* 1997; 127: 1198-1205; Liu J, et al. "Isolation of linoleic acid as an estrogenic compound from the fruits of Vitex agnus-castus L. (chaste-berry)." *Phytomedicine* 2004; 11(1):18-23; Westphal et al. "A nutritional supplement for improving fertility in women: a pilot study." *Journal of Reproductive Medicine* 2004; 49(4):289-93.

See also U.S. Pat. Nos. 6,852,757; 6,762,313; 6,756,405; 6,743,931; 6,610,868; 6,608,222; 6,524,527; 6,440,931; 6,420,577; 6,410,761; 6,409,649; 6,395,782; 6,333,353; 6,319,950; 6,300,374; 6,296,861; 6,242,621; 6,153,774; 5,892,074; 5,443,844; 4,529,551; and 4,281,064.

SUMMARY OF THE INVENTION

Methods and compositions for enhancing the probability that a subject will become pregnant are provided. In practicing the subject methods, an effective amount of a linoleic acid agent, such as linoleic acid or a PUFA analog thereof, is administered to the subject, e.g., via oral, intravaginal, intrauterine, or rectal administration routes. Also provided are compositions and kits that find use in practicing the subject methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DESCRIPTION OF REPRESENTATIVE EMBODIMENTS OF THE INVENTION

Methods and compositions for enhancing the probability that a subject will become pregnant are provided. In practicing the subject methods, an effective amount of a linoleic acid agent, such as linoleic acid or a PUFA analog thereof, is administered to the subject, e.g., via oral, intravaginal, intrauterine, or rectal administration routes. Also provided are compositions and kits that find use in practicing the subject methods.

In further describing aspects of the invention in greater detail than provided in the Summary and as informed by the Background and Definitions provided above, representative methods are described first in greater detail, followed by a review of representative applications in which the methods find use, as well as in a discussion of systems and kits that find use in practicing the subject methods.

Methods

As summarized above, the subject invention provides methods for enhancing the probability that a subject will become pregnant. In other words, the subject invention provides methods for increasing the chances that a given subject will become pregnant following a fertilization event. The phrase "fertilization event" is used broadly to refer to a variety of different approaches by which a female may become pregnant, e.g., an insemination event, in which semen is introduced into the reproductive tract (e.g., genital tract) of a female or an implantation event in which a fertilized egg is introduced into the reproductive tract (e.g., uterus) of a female. By "enhancing the probability" or "increasing the chances" of becoming pregnant is meant that the odds of the subject becoming pregnant following an insemination event are increased by at least about 5%, such as at 10%, including at least about 25%, at least about 50%, at least about 75% etc., and in certain embodiments at least about 2-fold, such as at least about 5-fold, including at least about 10-fold or more, as compared to a control, e.g., where the subject has not been treated according to the subject invention.

A feature of the subject methods is that an effective amount of a linoleic acid active agent is administered to the subject to obtain the enhanced probability for the subject becoming pregnant. Linoleic acid ($C_{18}H_{32}O_2$) is a polyunsaturated fatty acid (PUFA) of the omega-6 series. The phrase "linoleic acid active agent" refers to linoleic acid, as well as analogues thereof, such as PUFA analogs, e.g., conjugating linoleic acids, etc. A variety of different representative linoleic acid active agents and methods for their fabrication are reviewed in U.S. Pat. Nos. 6,852,757; 6,762,313; 6,756,405; 6,743,931; 6,610,868; 6,608,222; 6,524,527; 6,440,931; 6,420,577; 6,410,761; 6,409,649; 6,395,782; 6,333,353; 6,319,950; 6,300,374; 6,296,861; 6,242,621; 6,153,774; 5,892,074; 5,443,844; 4,529,551; and 4,281,064; the disclosures of which are herein incorporated by reference. While not wishing to be bound by any particular theory, linoleic acid and its analogs act through multiple mechanisms, either systemically or locally, as a pro-estrogenic agent to regulate the hypothalamic-pituitary hormonal axis for subjects suffering from deficiencies or irregularities. Linoleic acid and its analogs also act through immunomodulation, by shifting the balance of activity from Th1 to Th2. This shift provides additional protection for the sperm as they proceed towards the ovum, as well as for the fertilized ovum's movement, subsequent implantation, and growth.

The compounds of the present invention can be applied by any of the accepted modes of systemic administration including oral, intravaginal, intrauterine, rectal (intrarectally), and otherwise systemic routes of administration. Any pharmaceutically acceptable mode of administration can be used, including solid, semi-solid, or liquid dosage forms, such as for example, tablets, suppositories, pills, capsules, powders, liquids suspensions, or the like, preferably in unit dosage form suitable to single administration of precise dosages, or in sustained or controlled release forms for the prolonged administration of the compound at a predetermined rate. The compositions typically include a conventional pharmaceutical carrier or excipient and the active agent and, in addition, can include other medicinal agents, pharmaceutical agents, carriers, etc. The compositions are advantageously compounded into unit dosage forms, containing a predetermined, standard amount of the active compound, to make dosing and patient compliance simpler.

The amount of active compound administered depends on the subject being treated, the severity of the affliction, the manner of administration and the judgment of the prescribing physician. However, an effective oral dosage is in general in the range of 100 mg to 5 g/day, which may be administered all at a time or in divided doses. An effective intravaginal dosage is in general in the range of 100 mg to 30 grams, which may be administered all at a time or in divided doses. The dosage of these compounds may vary in accordance with the administration route, the age of the patient and the degree of the therapeutic effect desired.

In representative embodiments, the compounds of the present invention are administered in the form of a pharmaceutical composition that contains them in admixture with a pharmaceutical carrier. The pharmaceutical composition can be in the dosage forms such as tablets, capsules, granules, fine granules, powders, syrups, suppositories, injections, or the like. These preparations can be prepared by conventional methods.

The carriers useful for these preparations include all organic or inorganic carrier materials that are usually used for the pharmaceutical preparations and are inert to the active ingredient. Examples of the carriers suitable for the preparation of tablets capsules, granules and fine granules are diluents such as lactose, starch, sucrose, D-mannitol, calcium sulfate, or microcrystalline cellulose; disintegrators such as sodium carboxymethylcellulose, modified starch, or calcium carboxymethylcellulose; binders such as methylcellulose, gelatin, acacia, ethylcellulose, hydroxypropylcellulose, or polyvinylpyrrolidone; lubricants such as light anhydrous silicic acid, magnesium stearate, talc, or hydrogenated oil; or the like. When formed into tablets, they may be coated in a conventional manner by using the conventional coating agents such as calcium phosphate, carnauba wax, hydroxypropyl methylcellulose, macrogol, hydroxypropyl methylphthalate, cellulose acetate phthalate, titanium dioxide, sorbitan fatty acid ester, or the like.

Examples of the carriers suitable for the preparation of syrups are sweetening agents such as sucrose, glucose, fructose, or D-sorbitol; suspending agents such as acacia, tragacanth, sodium carboxymethylcellulose, methylcellulose, sodium alginate, microcrystalline cellulose, or veegum; dispersing agents such as sorbitan fatty acid ester, sodium lauryl sulfate, or polysorbate 80; or the like. When formed into syrups, the conventional flavoring agents, aromatic substances, preservatives, or the like may optionally be added thereto. The syrups may be in the form of dry syrup that is dissolved or suspended before use.

Examples of bases used for the preparation of suppositories are cacao butter, glycerin saturated fatty acid ester, glycerogelatin, macrogol, or the like. When formed into suppositories, the conventional surface active agents, preservatives or the like may optionally be admixed.

When formed into preparations for intravaginal or intrauterine use, the compound is dissolved in distilled water, to which may optionally be added the conventional solubilizers, buffering or pH adjusting agents, isotonic agents, preservatives and other suitable substances. The injections or preparations for intravaginal or intrauterine use can be in the solid dry preparations, which are dissolved before use.

In representative embodiments, these pharmaceutical compositions contain linoleic acid as the active ingredient in an amount of about 0.5% by weight or more, such as from about 50 to 99% by weight, based on the total weight of the composition. These compositions may optionally contain other therapeutically active compounds.

For solid compositions, conventional non-toxic carriers include, for example mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol as a carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like to thereby form a solution or suspension. If desired, the pharmaceutical composition to be administered may also contain minor amounts of non-toxic auxiliary pH buffering agents and the like, for example, sodium acetate, sorbitan monolaurate, triethanolamine oleate, etc. Actual methods of preparing such dosage forms are known, or will be apparent to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.25 is to 99% with the balance made up from non-toxic carrier may be prepared. For oral administration, a pharmaceutically acceptable non-toxic composition is formed by the incorporation of any of the normally employed excipients, and may contain 1%-95% active ingredient, preferably 5%-90%.

For delayed release, the compounds of the invention may be formulated in a pharmaceutical composition, such as in microcapsules formed from biocompatible polymers, or in liposomal carrier systems according to methods known in the art.

Intravaginal or intrauterine administration is generally characterized by injection and/or placement with a carrier material, such as a tampon, catheter, syringe, cannula, or other method through the vagina or cervix. The materials can be prepared in conventional forms, either as liquid solutions, suspensions, or emulsions. Suitable excipients include, for example, water, saline, aqueous dextrose, glycerol, ethanol or the like. In addition, the pharmaceutical compositions may also contain minor amounts of non-toxic substances such as wetting or emulsifying agents, auxiliary pH buffering agents and the like, such as, sodium acetate, sorbitan monolaurate, triethanolamine oleate, etc.

For continuous release of active agent, the compound may be covalently conjugated to a water soluble polymer, such as a polylactide or biodegradable hydrogel derived from an amphipathic block copolymer, as described in U.S. Pat. No. 5,320,840. Collagen-based matrix implants, such as described in U.S. Pat. No. 5,024,841, are also useful for sustained delivery of therapeutics.

The method of the present invention can be used with other therapeutic agents commonly used to treat infertility, thus enhancing the effects of therapeutic agents and adjunctive agents. Other therapeutic agents used include clomiphene citrate and GnRH.

In representative embodiments of the inventions, the methods are characterized in that the linoleic acid active agent is not administered to the subject in the form of an extract of a naturally occurring source, e.g., plant source. As such, in these particular embodiments of the methods, the linoleic acid is not administered as an extract or other fraction of a plant. In these embodiments, where the linoleic acid active agent is obtained from a naturally occurring source, it is combined with a pharmaceutically acceptable delivery vehicle in a manner such that it is not considered by those of skill in the art to be an extract. In such embodiments, the linoleic acid active agent may be the sole active agent in the administered composition.

As noted above, in pharmaceutical dosage forms, a given pharmacological agent may be administered alone or with or in appropriate association, as well as in combination, with other pharmaceutically active compounds. As used herein, "administered with" means that a given pharmacological agent and at least one other adjuvant (including one or more other different pharmacological agents) are administered at times sufficiently close that the results observed are indistinguishable from those achieved when the pharmacological agent and at least one other adjuvant are administered at the same point in time. The pharmacological agent and at least one other adjuvant may be administered simultaneously (i.e., concurrently) or sequentially. Simultaneous administration may be carried out by mixing a given pharmacological agent and at least one other adjuvant prior to administration, or by administering a given pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that a given pharmacological agent and at least one other adjuvant are administered at the same point in time or immediately following one another. In the latter case, the pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent(s) calculated in an amount sufficient to produce the desired effect in association with a pharmaceutically acceptable diluent, carrier or vehicle. The specifications for the unit dosage forms of a given pharmacological agent employed in the practice of the present invention depend on, for example, the particular pharmacological agent employed and the effect to be achieved, the pharmacodynamics associated with the particular pharmacological agent in the subject, etc.

As noted above, those of skill in the art will readily appreciate that dose levels may vary as a function of the specific pharmacological agent, the nature of the delivery vehicle, and the like. Dosages for a given pharmacological agent are readily determinable by those of skill in the art by a variety of means. Exemplary dosage levels are provided herein and are not to be construed to limit the scope of the invention in any manner.

As noted above, embodiments include administering an effective amount of a first pharmacological agent and an effective amount of at least a second, different pharmacological agent, e.g., concurrently administered, where the two may differ in one or more of a variety of aspects, e.g., dosage, type, route of administration, etc. For example, embodiments may include administering a first type of pharmacological agent and at least one other type of pharmacological agent to provide an enhanced therapeutic effect. By "enhanced therapeutic effect" is meant that at least the initial relief of the particular fertility condition being treated by the first pharmacological agent employed occurs more quickly with a combination of the first pharmacological agent and at least one other different pharmacological agent, as compared to the same doses of each component given alone, or that doses of one or all component(s) are below what would otherwise be a minimum effective dose (a "sub-MED").

Accordingly, in practicing the subject methods, an effective amount of a pharmacological agent is administered to a subject to enhance the probability that the subject will become pregnant following a fertilization event. As noted above, the particular dosage, mode of administration, treatment times, etc., will vary according to a variety of factors, but will generally fall within the ranges conventionally administered for the particular pharmacological agent employed. As noted above, the dose of pharmacological agent will be different for different subject, condition(s) treated, etc.

The following descriptions of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent.

In certain embodiments, a given pharmacological agent may be administered at or near the time of a particular phase of a subject's menstrual cycle, i.e., in close temporal proximity to, including during, one or more phases of a subject's menstrual cycle. For example, embodiments of the subject methods may include administration of a pharmacological agent during at least a portion of the menses phase and/or follicular phase and/or the ovulation phase and/or the luteal phase. Of interest is the administration of a pharmacological agent at least near the time of, or during at least a portion of, the luteal phase. For example, embodiments may include administering at least one pharmacological agent during the luteal phase, after ovulation.

Embodiments of the subject invention may include observing (including measuring) one or more physiological or biologic aspects of a subject and employing the observed one or more aspects as an indicator of the state of the immune system and Th1/Th2 ratio. Stated otherwise, embodiments include a closed-loop system in which a variable is used as an indicator of state of the immune system and may be employed as a trigger to initiate, terminate or adjust modulation of the Th1/Th2 immune activity ratio in a manner to treat a subject for infertility. A variable may be measured and the Th1/Th2 immune activity ratio may be modulated in a manner to alter the variable. Once a predetermined target variable measurement is achieved, modulation may be terminated.

For example, in the case where pulmonary gas is monitored before and/or during and/or after Th1/Th2 immune activity modulation, the particulars of a pharmacological modulation may be based on the determined pulmonary gas levels such that the amount of pharmacological agent may be continually or periodically adjusted until a predetermined, e.g., normal, pulmonary gas level is obtained, at which time Th1/Th2 immune activity modulation may be terminated. For example, the dosage of a given agent may be based on a determined pulmonary gas level. This monitoring and modulation of Th1/TH2 immune activity may be performed automatically, e.g., by way of suitable componentry such that a physiological aspect of a subject may be repeatedly monitored a given Th1/Th2 immune activity ratio modulation protocol and may be adjusted one or more times based on the results of the monitoring. In many embodiments, an Th1/Th2 immune activity ratio modulation protocol may be continued until a particular level or quality of one or more physiological or biologic aspects are obtained, i.e., a predetermined parameter may be targeted and the Th1/Th2 immune activity ratio may be modulated until that predetermined parameter is achieved. In certain embodiments, a targeted level or quality of a physiological and/or biologic aspect is analogous to the level or quality of a normal subject, as described above. In the below-described exemplary physiological aspects that may be employed in such a feedback loop system, reference values are indicated in parenthesis such that in certain embodiment a reference value may be a target value and once observed, modulation of the Th1/Th2 immune activity ratio may be terminated. Accordingly, in certain embodiments a given Th1/TH2 immune activity ratio modulation protocol may be performed until a time at which a predetermined level or quality of a physiological aspect or biologic aspect of a subject is observed, such as a reference value.

Any suitable method may be employed for such observing, determining and monitoring where such methods are known in the art and include methods described herein.

In certain embodiments, the determination of pulmonary gases may be employed (reference: alveolar oxygen 600-713 mm Hg).

In certain embodiments, the determination of serum blood gases may be employed (reference: ph range 7.1 to 7.7; arterial $pCO_2$ range 10 mm Hg to 80 mm Hg; arterial $pO_2$ range from 50 mmHg to 110 mmHg; arterial bicarbonate range 10 meq to 40 meq/L; alveolar/oxygen ratio of 1.0 to 0.6; alveolar to arterial gradient of 5 to 120 mHg; venous oxygen saturation 30% to 80%).

In certain embodiments aspects measured during an overnight sleep study may be employed. Sleep study parameters include, but are not limited to the following: sleep state (EEG leads); electrooculogram; EMG; airflow at nose and mouth (via thermistor, capnography, mask and pneumotachygraph, or other methods); chest and abdominal wall motion (impedance or inductance plethysmography or other); electrocardiogram; pulse oximetry including pulse waveform; end tidal carbon dioxide; video camera monitoring with sound montage; transcutaneous oxygen and carbon dioxide tensions; nasal pressure flow measurements; esophageal manometry; continuous noninvasive blood pressure monitoring; autonomic nervous system tone using finger tonometry.

In certain embodiments, the determination of cardiopulmonary physiological parameters may be employed that such as, but not limited to: cardiac output (reference: 1 to 6 L/min); cardiac index (reference: 0.5 to 6 L/min/m2); central venous pressure (reference: 3 to 30 cm H$_2$O); right arterial pressure (reference: 1-30 mm Hg); right to ventricular systolic pressure (reference: 5 to 50 mm Hg); right ventricular diastolic pressure (reference: 1 to 50 mm Kg); pulmonary arterial systolic pressure (reference: 5 to 50 mm Hg,); pulmonary arterial diastolic pressure (reference: 1 to 30 mm Hg); mean pulmonary arterial pressure (reference: 5 to 50 mm Hg); pulmonary capillary wedge pressure (reference: 1 to 20 mm Hg).

In certain embodiments, the determination of pulmonary function and spirometry parameters may be employed that such as, but not limited to: tidal volume (reference: 2 mL/kg to 20 ml/kg or 20-80% of predicted); total lung capacity or TLC (reference: 3 to 10 liters or 20-120% of predicted); residual volume (reference: 0.5 to 5 L or 20-120% of predicted); forced expiratory volume in 1 second or FEV1 (reference: 0.5 to 6 liters or 20-120% of predicted); functional vital capacity or FVC (reference: 0.5 to 6 liters or 20-120% of predicted); FEV1/FVC ratio (reference: 20-120%); forced expiratory flow or FEF 25-75 (reference: 50 to 150%); peak expiratory flow rate (reference: 60-120%); forced expiratory time (reference: 0-20 seconds); corrected diffusion capacity or DLCO (reference: 60-140%); corrected QT interval (reference: less than about 600).

Sleep study parameters that may be employed include, but are not limited to: sleep latency (reference: 0-1 hour); total sleep time (reference: 0-12 hours); percent REM sleep (reference 0-40% total sleep time); percent stage 3-4 non-REM sleep (reference 0-50% of total sleep time); respiratory arousal index (reference 0-40/hour total sleep time); periodic leg movements (reference 0-40/hour total sleep time); apnea index (reference 0-20/hour of total sleep time); hypopnea index (reference 0-40/hour of total sleep time); nadir oxygen saturation (reference 40-100%); mean oxygen saturation (reference 40-100%); desaturation index (reference 0-40 defined as >4% for 5 seconds/hour of total sleep time); highest carbon dioxide (reference 10 to 80 mmHg); carbon dioxide >45 mm Hg (reference 0-60% of total sleep time).

In certain embodiments, the determination of serum markers may be employed such as, but not limited to: catecholamine levels; acetylcholine levels (reference 300-2000 IU/L); aldosterone levels (reference 5-150 nmol/day); renin levels (reference 3-200 uU/mL); vasopressin levels (reference 1-20 pg/ml); angiotensin converting enzyme levels (reference 5-200 U/L); interleukin 1-3 and 5-13 and 18; interleukin-4; interferon alpha and beta; interferon gamma; tumor necrosis factor alpha; transforming growth factor; hemoglobin A1C (reference 2.0-12%); fasting glucose (reference fasting 1.0-10.0 mmol/L); high density lipoprotein (10-90); low density lipoprotein (60-200); triglyceride (reference 0.5 to 4.0 mmol/L); beta natriuretic peptide (reference 0-100 pg/mL); alpha natriuretic peptide (reference 0-50 pg/mL); erthythrocyte sedimentation is rate (ESR) (reference 1-200 mm/Hour); C-reactive protein (CRP) (reference 1-80 mg/L); transferrin (reference 0.5 to 6 g/L); hemoglobin (reference normal hemoglobin is 25 to 300 gm/L); hematocrit (reference 25-60%); ferritin (reference 5 to 600 pg/L); iron (reference 5 to 100 μmol/L); cholinesterase (reference −200-2500 IU/L); urine adrenaline (reference adrenaline 0-200 nmol/day); unrine noradrenaline (reference 0-1600 nmol/day); urine dopamine (reference 0-7000 nmol/day); adrenocorticotrophic hormone (ACTH) (reference 0 to 40 μmol/L); antidiuretic hormone (reference 1-20 pg/mL); thrombin clotting time (reference −5-30 seconds); serum total cholesterol (reference 100-300); and the like.

Other physiologic or biologic aspects include, but are not limited to: body mass index (reference <40); systolic blood pressure (reference 90-180 mmHg); diastolic blood pressure (30-100 mmHg); pulse pressure (reference 20-40 mmHg); heart rate (reference 30-150 beats/min in adults); corrected QT interval (reference <600); increasing heart rate variability; increasing respiratory sinus arrhythmia; and the like.

In certain embodiments, based the observed measurement of one or more of the above, Th1/Th2 immune activity ratio modulation may be initiated, altered or terminated to treat a subject for a condition. In this manner, continual adjustments may be made to tailor a treatment protocol to a particular physiological or biological state of a subject.

Where desired, the subject methods typically include determining (e.g., predetermining) the occurrence of one or more phases of a subject's menstrual cycle by any suitable method, e.g., using hormone-specific blood tests, urine tests, etc., as is known to those of skill in the art. For example, the onset of the luteal phase may be determined using a urine leutinizing hormone ("LH") detection test or kit, as are known in the art, e.g., as available under the brand names OVUQUICK ONE-STEP™, CLEARPLAN EASY™ and SURESTEP™. Other methods of determining the onset, duration, end, etc., of a given menstrual phase may be employed and include empirical and non-empirical methods, e.g., calendar methods (counting days), estimating the start, duration and/or end of a particular menstrual cycle phase, and the like. Regardless of the particular method employed, the onset of ovulation and/or the luteal phase may be determined and one or more of the pharmacological agents described above may be administered at or near the determined start of the subject's luteal phase and/or during at least part of a subject's determined luteal phase, including all days of the subject's luteal phase.

A feature of embodiments of the invention is that the subject that is being treated is one that has been diagnosed or predetermined, e.g., by a health care professional, to have difficulty in becoming pregnant, e.g., has an infertility condition, as reviewed in greater detail below.

Certain embodiments of the subject methods include a step of testing whether the subject is pregnant following a given period of time, e.g., at least about 2 days, such as at least about 1 week, at least about 2 weeks, etc., following a fertilization event. Such testing may include use of any convenient assay, including over the counter pregnancy detection assays available under a variety of different trademarks and from a variety of different manufacturers.

As reviewed above, the subject methods enhance the probability that a subject will become pregnant. A given method is considered to fall within the scope of the invention if it results in an increase in the number of pregnancies occurring following a fertilization event in a test population of least 100, such as at least 1000 individuals, of at least about 5% or more, such as at least about 10% or more, including at least about 25% or more, e.g., at least about 50% or more, as compared to a suitable control (e.g., same study but with administration of a placebo instead of a linoleic acid active agent).

Utility

The subject methods find use in a variety of applications in which it is desired to enhance the probability that a subject will become pregnant. In representative applications, the subject methods are employed to treat a subject for a fertility condition.

Infertility derived from the female partner has many overlapping subtypes, which include corpus luteum deficiency, polycystic ovarian syndrome, progesterone deficiency, anovulation, structural abnormalities of the female genital tract, endometriosis, and others. The subject methods find use in the treatment of a variety of different fertility conditions; including, but not limited to, infertility, subfertility, early pregnancy loss, spontaneous abortion, implantation failure, amenorrhea, luteal insufficiency (also referred to as luteal phase defect ("LPD")), dysmenorrhea (also referred to as pelvic pain, menstrual cramps, and the like), chemical pregnancy loss, stillbirth, habitual abortion, endometriosis, and the like. Infertility is defined broadly as the inability to conceive a child despite trying for one year during which there has been intercourse and no use of contraception. Subfertility is defined broadly as the inability to conceive a child after two years during which there has been intercourse and no use of contraception. Early pregnancy loss is defined broadly as the termination of pregnancy without human interference before 20 weeks gestation or below a fetal weight of 500 grams. Spontaneous abortion is defined broadly as the loss of fetus without human interference implantation failure is defined broadly as failure of a fertilized egg to implant. Amenorrhea is defined broadly to include the absence of a menstrual period and includes women who have not had a period in their teenage years and women who used to have a regular period that has stopped. Luteal insufficiency is defined broadly as hormonal imbalance during the luteal phase which interferes with fertility. Dysmenorrhea is defined broadly as menstrual cramps. Chemical pregnancy loss is defined broadly as loss of a biochemically evident pregnancy. Stillbirth is defined broadly as pregnancy loss after 20 weeks gestation; neonatal loss is the death of a liveborn fetus. Habitual or recurrent abortion is defined broadly as three or more consecutive abortions. Endometriosis is defined broadly as a condition in which endometrial tissue, the tissue that lines the inside of the uterus, grows outside the uterus and attaches to other organs in the abdominal cavity such as the ovaries and fallopian tubes.

By "treatment" is meant that at least an amelioration of the symptoms associated with the condition afflicting the subject is achieved, where amelioration is used in a broad sense to refer to at least a reduction in the magnitude of a parameter, e.g., associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition.

A variety of subjects are treatable according to the subject methods. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans and particularly female humans. As the subject methods are employed to treat fertility disorders, female, humans subjects of child-bearing age may be treated according to the present invention. While the present invention may be used for the treatment of a human, female subject, it is to be understood that the subject methods may also be carried-out on other female animal subjects such as, but not limited to, mice, rats, dogs, cats, livestock and horses, etc. Accordingly, it is to be understood that any female subject in need of being treated according to the subject invention is suitable.

Moreover, suitable subjects of this invention include those who have and those who have not previously been afflicted with a fertility condition, those that have previously been determined to be at risk of suffering from a fertility condition, and those who have been initially diagnosed or identified as being afflicted with or experiencing a fertility condition.

Kits

Also provided are kits for practicing the subject methods. The subject kits may vary greatly in regards to the components included depending on the particular condition treated, etc. For example, kits may include one or more pharmacological agents in suitable form(s). A given pharmacological agent may be present in a kit in varying dosages. A kit may also include more than type of pharmacological agent. The dosage amount of the one or more pharmacological agents provided in a kit may be sufficient for a single application or for multiple applications. In certain embodiments, multiple dosage amounts of a pharmacological agent may be present in a kit. In those embodiments having multiple dosage amounts, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit may be dictated by the particular pharmacological agent employed, as describe above, e.g., the particular form of the agent such as whether the pharmacological agent is formulated into preparations in solid, semi solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intravaginal, endocervical, intrathecal, intranasal, intravesicular, on the eye, in the ear canal, intraperiactivityal, intradermal, transdermal, intracheal, etc. Accordingly, certain systems may include a suppository applicator, syringe, I.V. bag and tubing, electrode, transdermal patch or film, etc.

Kits may also include diagnostic or detection tests for detecting the occurrence or onset of a particular phase of a subject's menstrual cycle, e.g., by determining certain hormone levels, including relative hormone levels. For example, a urine leutinizing hormone ("LH") detection test or kit or the like may be present in a kit. Urine LH detection kits are known in the art, e.g., OVUQUICK ONE-STEP, CLEARPLAN EASY and SURESTEP brand detection tests.

Kits may also include one or more pregnancy tests for determining whether a female is pregnant or not. For example, a pregnancy test may allow detection of a small amount of a certain hormone, e.g., hCG, as an indicator of pregnancy. Such test may conveniently be a home pregnancy test, where a variety of such tests are currently marketed under a variety of different trade marks from a variety of different manufacturers.

In certain embodiments, the kits include an assay for determining a Th1/Th2 immune activity ratio in a subject, as reviewed above.

The subject kits may also include instructions for how to practice the subject methods. For example, instructions may include how to administer the one or more pharmaceutical agents provided in the kit to treat a subject for a fertility condition by pharmacologically modulating at least a portion of the subject's autonomic nervous system. Instructions may include how to use an energy supplying device provided in the kit to treat a subject for a fertility condition by electrically modulating at least a portion of the subject's autonomic nervous system. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

The following examples further illustrate the present invention. These examples are intended merely to be illustrative of the present invention and are not to be construed as being limiting.

EXAMPLES

Example 1

Methods

Several patients from an active infertility clinic population are selected for open-label treatment with linoleic acid. All female patients have been unable to achieve a successful pregnancy for at least six months. Linoleic acid is formulated into a pharmaceutical oral form at a dosage of 100 mg-5 g/day for three months.

Results:

Successful pregnancies are seen in at least one patient who underwent this dose regimen, supporting the pharmaceutical use of linoleic acid to treat infertility.

Example 2

Methods

An animal model is used to determine the effects of linoleic acid on immune function of the uterine lining. Linoleic acid is delivered via several different methods—direct injection of the linoleic acid formulation into the vagina, direct injection of linoleic acid formulation into the uterus, linoleic acid soaked into a sponge and placed into the vagina. Control animals have sterile saline instilled in place of linoleic acid. The animals are then sacrificed, and the uterine lining is analyzed for changes in immunologic activity.

Results:

Changes in Th1/Th2 balance are seen in the linoleic acid-treated animals in comparison to the control animals.

It is evident from the above discussion that the above described invention provides important new ways to treat variety of different fertility conditions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of increasing the probability that a mammalian subject will become pregnant, said method comprising:
    administering to said mammalian subject a pharmaceutical composition comprising a linoleic acid active agent as the sole active agent in an amount effective to increase the probability that said mammalian subject will become pregnant.

2. The method according to claim 1, wherein said linoleic acid active agent is linoleic acid.

3. The method according to claim 1, wherein said linoleic acid active agent is conjugated linoleic acid.

4. The method according to claim 1, wherein said linoleic acid active agent is a linoleic acid analogue.

5. The method according to claim 1, wherein said linoleic acid analogue is a polyunsaturated fatty acid.

6. The method according to claim 1, wherein said effective amount of linoleic acid active agent ranges from about 100 mg to about 20 g/day.

7. The method according to claim 6, wherein said effective amount of linoleic acid active agent ranges from about 100 mg to about 5 g/day.

8. The method according to claim 1, wherein said pharmaceutical composition is orally administered to said mammalian subject.

9. The method according to claim 1, wherein said pharmaceutical composition is administered via intrauterine administration to said mammalian subject.

10. The method according to claim 1, wherein said pharmaceutical composition is administered via intravaginal or intrarectal administration to said mammalian subject.

11. The method according to claim 1, wherein said pharmaceutical composition is administered via injectible administration to said mammalian subject.

12. The method according to claim 1, wherein said effective amount of linoleic acid active agent is selected based at least in part on an observed measure of Th1/Th2 immune activity ratio in said mammalian subject.

13. The method according to claim 1, wherein said method comprises administering a dosage of said linoleic acid active agent to said mammalian subject a plurality of times comprising at least a first time and a second time.

14. The method according to claim 13, wherein the dosage of said linoleic acid active agent is changed between said first time and said second time.

15. The method according to claim 13, wherein a different linoleic acid active agent is administered to said mammalian subject at said first time and said second time.

16. The method of claim 13, wherein administration of dosages of said linoleic acid active agent is initiated or terminated when a predetermined measure of Th1/Th2 immune activity ratio is observed in said mammalian subject.

17. The method according to claim 1, wherein said mammalian subject is a female subject.

18. The method according to claim 17, wherein said female subject is a female human.

19. The method according to claim 1, wherein said probability is increased by at least about 10%.

20. The method according to claim 1, wherein said method is a method of treating a mammalian subject for infertility.

21. The method according to claim 1, wherein said method further comprises determining whether said mammalian subject is pregnant following administration of said linoleic acid active agent.

22. The method according to claim 21, wherein said determining comprises employing a home pregnancy assay.

\* \* \* \* \*